United States Patent
Pawliszyn (10) Patent No.: US 9,891,150 B2
(45) Date of Patent: Feb. 13, 2018

(54) METHOD FOR MEASURING OR IDENTIFYING A COMPONENT OF INTEREST IN A BIOLOGICAL SYSTEM

(71) Applicant: Janusz B. Pawliszyn, Waterloo (CA)

(72) Inventor: Janusz B. Pawliszyn, Waterloo (CA)

(73) Assignee: JP Scientific Limited, Waterloo (CA)

( * ) Notice: Subject to any disclaimer, the term of this patent is extended or adjusted under 35 U.S.C. 154(b) by 0 days.

(21) Appl. No.: 14/839,529

(22) Filed: Aug. 28, 2015

(65) Prior Publication Data

US 2015/0369712 A1    Dec. 24, 2015

Related U.S. Application Data (60) Continuation of application No. 14/492,411, filed on Sep. 22, 2014, now abandoned, which is a division of application No. 13/478,295, filed on May 23, 2012, now abandoned, which is a division of application No. 12/174,494, filed on Jul. 16, 2008, now abandoned, which is a continuation-in-part of application No. 11/706,167, filed on Feb. 15, 2007, now Pat. No. 8,008,064, which is a continuation of application No. 11/208,933, filed on Aug. 23, 2005, now Pat. No. 7,232,689, which is a continuation-in-part of application No. 10/506,827, filed as application No. PCT/CA03/00311 on Mar. 6, 2003, now Pat. No. 7,384,794.

(60) Provisional application No. 60/364,214, filed on Mar. 11, 2002, provisional application No. 60/393,309, filed on Jul. 3, 2002, provisional application No. 60/421,001, filed on Oct. 25, 2002, provisional application No. 60/421,510, filed on Oct. 28, 2002, provisional application No. 60/427,833, filed on Nov. 21, 2002.

(51) Int. Cl.
| | | |
|---|---|---|
| *G01N 1/40* | (2006.01) | |
| *B01J 20/283* | (2006.01) | |
| *A61B 5/15* | (2006.01) | |
| *H01J 49/16* | (2006.01) | |
| *A61B 10/00* | (2006.01) | |
| *G01N 30/00* | (2006.01) | |
| *G01N 30/06* | (2006.01) | |

(52) U.S. Cl.
CPC ....... *G01N 1/405* (2013.01); *A61B 5/150358* (2013.01); *B01J 20/283* (2013.01); *H01J 49/165* (2013.01); *A61B 10/0045* (2013.01); *G01N 2030/009* (2013.01); *G01N 2030/062* (2013.01); *Y10T 428/2933* (2015.01)

(58) Field of Classification Search
CPC ............. G01N 1/405; G01N 2030/009; G01N 2030/062; A61B 5/150358; A61B 10/0045; B01J 20/283; H01J 49/165; Y10T 428/2933
See application file for complete search history.

(56) References Cited

U.S. PATENT DOCUMENTS

| | | | |
|---|---|---|---|
| 4,140,653 | A | 2/1979 | Imura et al. |
| 4,476,231 | A | 10/1984 | Deindoerfer |
| 4,616,652 | A | 10/1986 | Simpson |
| 5,047,437 | A | 9/1991 | Cooke et al. |
| 5,081,871 | A | 1/1992 | Glaser |
| 5,120,510 | A | 6/1992 | Gourley et al. |
| 5,424,187 | A | 6/1995 | Shor et al. |
| 5,460,813 | A | 10/1995 | Leung |
| 5,464,395 | A | 11/1995 | Faxon et al. |
| 5,479,923 | A | 1/1996 | Rantala |
| 5,640,470 | A | 6/1997 | Iyer et al. |
| 5,691,206 | A | 11/1997 | Pawliszyn |
| 5,693,228 | A | 12/1997 | Koehler et al. |
| 5,808,300 | A | 9/1998 | Caprioli |
| 6,027,942 | A | 2/2000 | Hutchens et al. |
| 6,042,787 | A | 3/2000 | Pawliszyn |

(Continued)

FOREIGN PATENT DOCUMENTS

| | | |
|---|---|---|
| CN | 2630850 Y | 8/2004 |
| CN | 102698720 | 10/2012 |
| DE | 19905239 | 8/2000 |
| EP | 1618592 | 1/2006 |
| JP | 1164277 | 5/1999 |
| WO | 9115745 | 10/1991 |
| WO | 0068665 | 11/2000 |
| WO | 2010008450 | 1/2010 |

OTHER PUBLICATIONS

Furlong et al. Routine determination of sulfonylurea, imidazolinone, and sulfonamide herbicides at nanogram-per-liter concentration by solid-phase extraction and liquid chromatography/mass spectrometry. Sci Total Environ 2000, vol. 248, pp. 135-146.*

(Continued)

*Primary Examiner* — Shafiqul Haq
(74) *Attorney, Agent, or Firm* — David Nauman; Borden Ladner Gervais LLP (57) ABSTRACT

A method for measuring or identifying a component of interest in a biological system is disclosed herein. The method includes positioning a fiber within the biological system, the fiber being at least partially coated with a polymeric extraction phase for adsorbing the component of interest from the biological system, the extraction phase being positioned within the biological system; adsorbing the component of interest onto the extraction phase; removing the fiber from the biological system; inserting the fiber into a nanospray needle; flowing solvent through the nanospray needle; desorbing the component of interest from the extraction phase into the solvent; and nanospraying the desorbed component of interest into an analytical instrument for measurement or identification.

16 Claims, 3 Drawing Sheets

(56) References Cited

U.S. PATENT DOCUMENTS

| | | |
|---|---|---|
| 6,287,521 B1 | 9/2001 | Quay et al. |
| 6,360,588 B1 | 3/2002 | Ross |
| 6,555,813 B1 | 4/2003 | Beecher et al. |
| 6,558,958 B1 | 5/2003 | Pilevar |
| 6,689,603 B2 | 2/2004 | Pompidou et al. |
| 6,730,096 B2 | 5/2004 | Basta |
| 6,743,180 B1 | 6/2004 | Van Bockel |
| 6,808,937 B2 | 10/2004 | Ligler |
| 6,871,556 B2 | 3/2005 | Andresen et al. |
| 7,019,288 B2 | 3/2006 | Becker |
| 7,125,580 B2 | 10/2006 | Miller et al. |
| 7,151,167 B2 | 12/2006 | Gierde et al. |
| 7,211,189 B2 | 5/2007 | Jinno et al. |
| 7,232,689 B2 | 6/2007 | Pawliszyn |
| 7,259,019 B2 | 8/2007 | Pawliszyn et al. |
| 7,384,794 B2 | 6/2008 | Pawliszyn |
| 7,468,281 B2 | 12/2008 | Kallury et al. |
| 7,479,390 B2 | 1/2009 | Pawliszyn |
| 7,537,803 B2 | 5/2009 | Wang et al. |
| 7,605,003 B2 | 10/2009 | Chan |
| 7,667,010 B2 | 2/2010 | Gierde et al. |
| 8,008,064 B2 | 8/2011 | Pawliszyn et al. |
| 8,148,161 B2 | 4/2012 | Higgins et al. |
| 8,206,902 B2 | 6/2012 | Mitani et al. |
| 8,362,219 B2 | 1/2013 | Gjerde et al. |
| 8,399,055 B2 | 3/2013 | Bakry et al. |
| 8,598,325 B2 | 12/2013 | Pawliszyn |
| 9,108,217 B2 | 8/2015 | Hoerr et al. |
| 9,502,226 B2 | 11/2016 | Brown et al. |
| 2002/0034827 A1 | 3/2002 | Singh et al. |
| 2003/0135195 A1 | 7/2003 | Jimenez et al. |
| 2003/0180954 A1 | 9/2003 | Riviere et al. |
| 2003/0183758 A1 | 10/2003 | Colburn et al. |
| 2004/0005582 A1 | 1/2004 | Shipwash |
| 2004/0171169 A1 | 9/2004 | Kallury et al. |
| 2004/0191537 A1 | 9/2004 | Lubda et al. |
| 2004/0224362 A1 | 11/2004 | Gjerde et al. |
| 2004/0241721 A1 | 12/2004 | Gjerde et al. |
| 2005/0032237 A1 | 2/2005 | Sandra et al. |
| 2005/0112650 A1 | 5/2005 | Chang et al. |
| 2005/0133714 A1 | 6/2005 | Vestal et al. |
| 2005/0142033 A1 | 6/2005 | Glezer et al. |
| 2008/0023630 A1 | 1/2008 | Boschelli et al. |
| 2008/0193772 A1 | 8/2008 | Agroskin et al. |
| 2009/0026122 A1 | 1/2009 | Pawliszyn et al. |
| 2009/0301169 A1 | 12/2009 | Higgins et al. |
| 2010/0130796 A1 | 5/2010 | Combes et al. |
| 2010/0144049 A1 | 6/2010 | Combes et al. |
| 2014/0017693 A1 | 1/2014 | Mao et al. |
| 2014/0346348 A1 | 11/2014 | Krechmer et al. |
| 2015/0068280 A1 | 3/2015 | Ricoul |
| 2015/0200083 A1 | 7/2015 | Brown et al. |
| 2015/0231602 A1 | 8/2015 | Pawliszyn |
| 2015/0318158 A1 | 11/2015 | Pawliszyn et al. |
| 2015/0318160 A1 | 11/2015 | Pawliszyn et al. |
| 2015/0364310 A1 | 12/2015 | Musselman |

OTHER PUBLICATIONS

Sigma-Aldrich, SPME sample prep made easy: how to choose the proper SPME fiber., Newsletter, 1999 Sigma-aldrich, Supelco, Supelco Park, Bellefonte, PA 16823.*

Chen et al. Solid phase microextraction coupled to high-performance liquid chromatography., Anal. CHem., 1995, vol. 67, pp. 2530-2533.*

Moder et al. Determination of urinary acylcarnitines by ESI-MS couple with solid-phase microextraction (SPME). J. Mass Spectrometry 1997, vol. 32, pp. 1195-1204.*

International Search Report and Written Opinion from corresponding PCT Application No. PCT/CA2015/050550 dated Aug. 27, 2015.

International Search Report and Written Opinion from corresponding PCT Application No. PCT/CA2015/050551 dated Aug. 27, 2015.

Deng et al., "Strategies for coupling solid-phase microextraction with mass spectometry", Trends in Analytical Chemistry, 55, pp. 55-67, Mar. 2014.

R.M. Gonzalez-Rodriguez, B. Cancho-Grande, and J. Simal-Gandara, Multiresidue determination of 11 new fungicides in grapes and wines by liquid-liquid extraction/clean-up and programmable temperature vaporization injection with analyte protectants/gas chromatography/ion trap mass spectrometry, Journal of Chromatography A, 2009, vol. 1216, pp. 6033-6042.

K. Banerjee, D.P. Oulka, S. Dasgupta, S.B. Patil, S.H. Patil, R. Savant, and P.G. Adsule, Validation and uncertainty analysis of a multi-residue method for pesticides in grapes using ethyl acetate extraction and liquid chromatography-tandem mass spectrometry, Journal of Chromatography A, 2007, vol. 1173, 1-2, pp. 98-109.

V. Guillet, C. Fave, and M. Montury, Microwave/SPME method to quatify pesticides residues in tomato fruits, Journal of Environmental Science and Health Part. B, 2009, vol. 44, pp. 415-422.

J. Oliva, A. Barba, N. Vela, F. Melendreras, and S. Navarro, Multiresidue method for the rapid determination of organophosphorous insecticides in grapes, must and wine, Journal of Chromatography A, 2000, vol. 882, pp. 213-220.

J. Oliva, S. Navarro, A. Barba, and G. Navarro, Determination of chlorpyrifos, penconazole, fenarimol, vinclozolin and metalaxyl in grapes, must and wine by on-line microextraction and gas chromatogaphy, Journal of Chromatography A, 1999, vol. 833, pp. 43-51.

A. J. A. Charlton, and A. Jones, Determination of imisazole and triazole fungicide residues in honeybees using gas chromatography-mass spectrometry, Journal of Chromatography A, 2007, 1141, pp. 117-122.

J. Zeng, J.i Chen, Z. Lin, W. Chen, X. Chen, and X Wang, Development of polydimethylphenylsiloxane-coated fiber for solid-phase microextraction and its analytical application of qualitative and semi-quantitative of organochlorine and pyrethroid pesticides in vegetables, Analytica Chimica Acta, 2008, vol. 619, pp. 59-66.

M. Anastassiades, S. J. Lehotay, D. Stajnbaher, and F. J. Schenck, Fast and easy multiresidue method employing acetonitrile extraction/partitioning and "dispersive solid-phase extraction" for the determination of pesticide residues in produce. Journal of AOAC International, 2003, vol. 86, 2, pp. 412-431.

D. Steiniger, G. P.Lu, J. Butler, E. Phillips, and Y. Fintschenko, Determination of Multiresidue Pesticides in Green Tea by Using a Modified QuEChERS Extraction and Ion-Trap Gas Chromatography/Mass Spectrometry, Journal of AOAC International, 2010, vol. 93, 4, pp. 1169-1179.

S. C. Cunha, J. O. Fernandes, A. Alves, and M.B.P.P. Oliveira, Fast low-pressure gas chromatography-mass spectrometry method for the determination of multiple pesticides in grapes, must and wines, Journal of Chromatography A, 2009, vol. 1216, pp. 119-126.

Wong J, C.Y. Hao, K. Zhang, P. Yang, K. Banerjee, D. Hayward, I. Iftakhar, A. Schreiber, K. Tech, C. Sack C, M. Smoker, X.R. Chen, S.C. Utture, and D.P. Oulka, Development and Interlaboratory Validation of a QuEChERS-Based Liquid Chromatography-Tandem Mass Spectrometry Method for Multiresidue Pesticide Analysis, Journal of Agricultural and Food Chemistry, 2010, vol. 58, 10, pp. 5897-5903.

P. Paya, M. Anastassiades, D. Mack, I. Sigalova, B. Tasdelen, J. Oliva, and A. Barba, Analysis of pesticide residues asing the Quick Easy Cheap Effective Rugged and Safe (QuEChERS) pesticide multiresidue method in combination with gas and liquid chromatography and tandem mass spectrometric detection. Analytical and Bioanalytical Chemistry, 2007, vol. 389, 6.

Pawliszyn and J. SPME Method Development. Solid Phase Microextraction: Theory and Practice, 1. New York : Wiley-VCH, 1997, pp. 97-139.

S. Risticevic, H. Lord, T. Gorecki, C. L. Arthur, and J. Pawliszyn, Protocol for solid phase microextraction method development, Nature Protocols, 2010, vol. 5, 1, pp. 122-139.

J. Schurek, T. Portoles, J. Hajslova, K. Riddellova, and F. Hernandez, Application of head-space solid-phase microextraction coupled to comprehensive two-dimensional gas chromatography-time-of- (56) References Cited

OTHER PUBLICATIONS flight mass spectrometry for the determination of multiple pesticide residues in tea samples, Analytica Chimica Acta, 2008, vol. 611, 2, pp. 163-172.
D. A. Lambropoulou and T. A. Albanis, Headspace solid-phase microextraction in combination with gas chromatography-mass spectrometry for the rapid screening of organophosphorus insecticide residues in strawberries and cherries, Journal of Chromatography A, 2003, vol. 993, 1-2, pp. 197-203.
M. Natangelo, S. Tavazzi, and E. Benfenati, Evaluation of solid phase microextraction-gas chromatography in the analysis of some pesticides with different mass spectrometric techniques: Application to environmental waters and food samples, Analytical Letters, 2002, vol. 35, 2, pp. 327-338.
W. Chen, KF Poon and M. H. W. Lam, The application of solid phase microextraction in the analysis of organophosphorous pesticides in a food plant, Environmental Science & Technology, 1998, vol. 32, 23, pp. 3816-3820.
K. Fytianos, N. Raikos, G. Theodoridis, Z. Velinova, and H. Tsoukali.,Solid phase microextraction applied to the analysis of organophosphorous insecticides in fruits, Chemosphere, 2006, vol. 65, pp. 2090-2095.
A. Menezes Filho, F, N. Santos, and P. A. P. Pereira, Development, validation and application of a maethodology based on solid-phase micro extraction followed by gas chromatography coupled to mass spectrometry (SPME/GC-MS) for the determination of pesticides residues in mangoes, Talanta, 2010, vol. 81, pp. 346-354.
M. Volante, M. Pontello, L. Valoti, M. Cattaneo, M. Bianchi, and L. Colzani, Application of solid phase microextraction (SPME) to the analysis of pesticides residues in vegetables, Pest Management Science, 2000, vol. 56, pp. 618-636.
H. L. V. Capobiango and Z. L Cardeal, A solid phase microextraction method for the chromatographic determination of organophosphorous pesticides in fish, water, potatoes, guava and coffee, Journal of Brazilian Chemical Society, 2005, vol. 16, 5, pp. 907-914.
C. G. Zambonin, M. Quinto, N. De Vietro, and F. Palmisano, Solid phase microextraction—gas chromatography mass spectrometry: A fast and simple screening method for the assessment of organophosphorous pesticides residues in wine and fruit juices. Food Chemistry, 2004, vol. 86, pp. 269-274.
C. G. Zambonin, A. Cilenti, F. Palmisano, Solid phase microextraction and gas chromatography-mass spectrometry for the rapid screening of triazole residues in wine and strawberries, Journal of Chromatography A, 2002, vol. 967, pp. 255-260.
A. Aguinaga, N, Campillo, P. Vinas, and M. Hemadez-Cordoba, Solid phase microextraction coupled to gas chromatography-mass spectrometry for the analysis of famoxadone in wines, fruits and vegetables, Spectroscopy Letters, 2009, vol. 42, pp. 320-326.
R. Hu, B. Hennion, L. Urruty, and M. Montury, Solid phase microextraction of pesticide residues from strawberries, Food Additives and Contaminants, 1999, vol. 16, 3, pp. 111-117.
P. Vinas, N. Campillo, N. Martinez-Castillo, and M. Hernandez-Cordoba, Method development and validation for strobilurin fungicides in baby foods by solid phase microextraction gas chromatography-mass spectrometry, Journal of Chromatography A, 2009, vol. 1216, pp. 140-146.
K. Ridgway, S. P. D. Lalljie, and R. M. Smith, Sample preparation techniques for the determination of trace residues and contaminants in food, Journal of Chromatography A, 2007, vol. 1153, pp. 36-53.
F. Augusto, E. Carasek. R. G. C. Silva, S. R. Rivellino, A. D. Batista, and E. Martendal, New sorbents for extraction and microextraction techniques, Journal of Chromatography A, 2010, vol. 1217, pp. 2533-2542.
L. Cai, S. Gong, M. Chen, and C. Wu, Vinyl crown ether as a novel radical crosslinked sol-gel SPME fiber for determination of organousphorous pesticides in food samples, Analytica Chimica Acta, 2006, vol. 559, pp. 89-96.
D. Djozan, M. Mahkam, and B. Ebrahimi, Preparation and biding study of solid phase microextraction fiber on the basis of ametryn-imprinted polymer—Application to the selective extraction of persistent triazine herbicides in tap water, rice, maize and onion, Journal of Chromatography A, 2009, vol. 1216, pp. 2211-2219.
E. Turiel, J. L. Tadeo, and A. Martin-Esteban, Molecularly imprinted polymeric fibers for solid phase microextraction. Analytical Chemistry, 2007, vol. 79, pp. 3099-3104.
C. Dietz, J. Sanz, and C. Camara, Recent developments in solid phase microextraction coatings and related techniques, Journal of Chromatography A, 2006, vol. 1103, pp. 183-192.
J. Beltran, F.J. Lopez, and F. Hernandez, Solid-phase microextraction in pesticide residue analysis, Journal of Chromatography A, 2000, vol. 885, pp. 389-404.
A. Jahnke and P. Mayer, Do complex matrices modify the sorptive properties of polydimethylsiloxane (PDMS) for non-polar organic chemicals, Journal of Chromatography A, 2010, vol. 1217, 29, pp. 4765-4770.
D. Vuckovic, R. Shirey, Y. Chen, L. Sidisky, C. Aurand, K. Stenerson, and J. Pawliszyn, In vitro evaluation of new biocompatible coatings for solid-phase microextraction: Implications for drug analysis and in vivo sampling applicatons, Analytica Chimica Acta, 2009, vol. 638, pp. 175-185.
L. S De Jager, G. A. Perfetti, and G. W. Diachenko, Analysis of tetramethylene disulfotetramine in foods using solid-phase microextraction-gas chromatography-mass spectrometry, Journal of Chromatography A, 2008, vol. 1192, pp. 36-40.
A. L. Simplicio and L. V. Boas, Validation of a solid-phase microextraction method for the determination of organophosphorous pesticides in fruits and fruit juice, Journal of Chromatography A, 1999, vol. 833, pp. 35-42.
A. Kloskowski and M. Pilarczyk, Membrane solid-phase microextraction—A new concept in sorbent preparation, Analytical Chemistry, 2009, vol. 81, pp. 7363-7367.
Frérot et al., "Solid-Phase Microextraction (SPME): A New Tool in Pheromone Identification in Lepidoptera", J. High Resolut. Chromatogr., 1997, vol. 20, pp. 340-342.
Heinze, "Ultramicroelectrodes in Electrochemistry", Angew. Chem. Int. Ed. Engl., 1993, 32, pp. 1268-1288.
Jackson et al., "Mass spectrometry for genotyping: an emerging tool for molecular medicine", Molecular Medicine Today, Jul. 2000, vol. 6, pp. 271-276.
Lavaud et al., "Optimal anticoagulation strategy in haemodialysis with heparin-coated polyacrylonitrile membrane", Nephrology Dialysis Transplantation, 2003, 18, pp. 2097-2104, available at http://ndt.oxfordjournals.org/cgi/content/abstract/18/10/2097V.
Lord et al., "Development and Evaluation of a Solid-Phase Microextraction Probe for in Vivo Pharmacokinetic Studies", Anal. Chem. Oct. 1, 2003, vol. 75, No. 19, pp. 5103-5115.
Moneti et al., "Solid-phase Microextraction of Insect Epicuticular Hydrocarbons for Gas Chromatographic/Mass Spectrometric Analysis", Rapid Communications in Mass Spectrometry, vol. II, 1997 pp. 857-862.
Namera et al., "Analysis of anatoxin-a in aqueous samples of solid-phase microextraction coupled to high-performance liquid chromatography with fluorescence detection and on-fiber derivatization", Journal of Chromatography A, 963, 2002, pp. 295-302.
Nie et al., "Preparation and Characterization of polyacrylonitrile-based membranes: Effects of internal coagulant on poly (acrylonitrile-co-maleic acid) ultrafiltration hollow fiber membranes", Desalination 160 (2004) pp. 43-50.
Communication from European Examining Division dated Jan. 24, 2007 from corresponding European Patent Application No. 03706179.3.
Communication from European Examining Division dated Dec. 17, 2007 from corresponding European Patent Application No. 03706179.3.
Communication from European Examining Division dated Apr. 29, 2008 from corresponding European Patent Application No. 03706179.3.
Intention to Grant from European Examining Division dated Aug. 19, 2008 from corresponding European Patent Application No. 03706179.3.

(56) References Cited

OTHER PUBLICATIONS

Non-Final Office Action dated Feb. 16, 2014 from the corresponding U.S. Appl. No. 14/492,411.
Smith et al., "Solid-Phase Microextraction as a Tool for Studying Volatile Compounds in Frog Skin", Chemistry and Ecology, 2000, vol. 17, pp. 215-225.
Whang et al., "Solid phase microextraction coupled to capillary electrophoresis", Anal. Commun., 1998, 35, pp. 353-356.
Yang et al., "Surface Modification and Blood Compatibility of Polyacrylonitrile Membrane with Immobilized Chitosan-Heparin Conjugate", Journal of Polymer Research 9: 2002, pp. 201-206, http://www.springerlink.com/content/m2878p248r41nk81/.
Zang et al.. "Solid-Phase Microextraction, Analytical Chemistry", vol. 66, No. 17, Sep. 1, 1994, pp. 844-853.
Non-final Office Action dated Apr. 4, 2011 from corresponding U.S. Appl. No. 12/939,360.
English translation of Japanese Office Action dated Feb. 10, 2009 from corresponding Appl. No. 574050/2003.
Shirey, Robert E., "Optimization of Extraction Conditions and Fiber Selection for Semivolatile Analytes Using Solid-Phase Microextraction", Journal of Chromatographic Science, Jul. 2000, vol. 38, pp. 279-288.
Lambropoulou et al., "Validation of an SPME method, using PDMS, PA, PDMS-DVD, and CW-DVB SPME fiber coatings, for analysis of organophosphorus insecticides in natural waters", Anal Bioanal Chem, 2002. vol. 374, pp. 932-941.
Mullett et al., "Direct Determination of Benzodiazepines in Biological Fluids by Restricted-Access Solid-Phase Microextraction", Anal. Chem., 2002, Vol, 74, pp. 1081-1087.
Mindrup, et al: "Improved Performance of SPME Fibers and Applications", SUPELCO 2001, Sigma-Aldrich Co. 2001, pp. 1-25.
Musteata, et al. "Biocompatible solid-phase microextraction coatings based on polyacrylonitrile and solid-phase extraction phases." Anal. Chem. 2007, vol. 79, pp. 6903-6911.
Musteata, Mihaela. "Biocompatible solid phase microextraction." Master Thesis, University of Waterloo, 2006. pp. i-xi and 1-70.
Wang, et al. "Surface confined ionic liquid as a stationary phase for HPLC., " Analyst 2006, vol. 131, pp. 1000-1005.
Non-final Office Action from U.S. Appl. No. 13/478,295 dated Feb. 11, 2015.
Restriction Requirement dated Oct. 9, 2014 from U.S. Appl. No. 13/478,295.
Boos et al. Alkyl-diol silica (ADS): restricted access precolumn packing for direct injection and coupled-column chromatography of biofluids. Fesenius J Anal Chem 1995, vol. 352, pp. 684-690.
Restriction Requirement dated Nov. 17, 2008 from corresponding U.S. Appl. No. 11/706,167.
Non-final Office Action dated Aug. 2, 2010 from corresponding U.S. Appl. No. 11/706,167.
Non-final Office Action dated Jan. 21, 2011 from corresponding U.S. Appl. No. 11/706,167.
Notice of Allowance dated Jun. 16, 2011 from corresponding U.S. Appl. No. 11/706,167.
Restriction Requirement dated Apr. 28, 2011 from corresponding U.S. Appl. No. 12/174,494.
Non-final Office Action dated Aug. 29, 2011 from corresponding U.S. Appl. No. 12/174,494.
Final Office Action dated Jan. 20, 2012 from corresponding U.S. Appl. No. 12/174,494.
Advisory Action dated Mar. 22, 2012 from corresponding U.S. Appl. No. 12/174,494.
Non-final Office Action dated Jun. 25, 2014 from corresponding U.S. Appl. No. 12/174,494.
Non-final Office Action dated Jun. 30, 2005 from corresponding U.S. Appl. No. 10/506,827.
Final Office Action dated Dec. 28, 2005 from corresponding U.S. Appl. No. 10/506,827.
Non-final Office Action dated May 30, 2006 from corresponding U.S. Appl. No. 10/506,827.
Final Office Action dated Oct. 26, 2006 from corresponding U.S. Appl. No. 10/506,827.
Non-final Office Action dated May 29, 2007 from corresponding U.S. Appl. No. 101506,827.
Final Office Action dated Oct. 18, 2007 from corresponding U.S. Appl. No. 10/506,827.
Notice of Allowance dated Jan. 30, 2008 from corresponding U.S. Appl. No. 10/506,827.
Restriction Requirement dated Oct. 28, 2005 from corresponding U.S. Appl. No. 11/206,804.
Non-final Office Action dated Jan. 9, 2006 from corresponding U.S. Appl. No. 11/206,804.
Final Office Action dated Jul. 12, 2006 from corresponding U.S. Appl. No. 11/206,804.
Non-final Office Action dated Jan. 12, 2007 from corresponding U.S. Appl. No. 11/206,804.
Notice of Allowance dated May 16, 2007 from corresponding U.S. Appl. No. 11/206,804.
Restriction Requirement dated Dec. 1, 2005 from corresponding U.S. Appl. No. 11/208,933.
Non-final Office Action dated Mar. 27, 2006 from corresponding U.S. Appl. No. 11/208,933.
Non-final Office Action dated Aug. 9, 2006 from corresponding U.S. Appl. No. 11/208,933.
Final Office Action dated Jan. 3, 2007 from corresponding U.S. Appl. No. 11/208,933.
Notice of Allowance dated Feb. 20, 2007 from corresponding U.S. Appl. No. 11/208,933.
Non-final Office Action dated Apr. 1, 2011 from corresponding U.S. Appl. No. 12/938,876.
Notice of Allowance dated Jan. 11, 2012 from corresponding U.S. Appl. No. 12/938,876.
Notice of Allowance dated Nov. 10, 2011 from corresponding U.S. Appl. No. 12/939,360.
Restriction Requirement dated Jan. 22, 2013 from corresponding U.S. Appl. No. 13/412,122.
Non-final Office Action dated Apr. 8, 2013 from corresponding U.S. Appl. No. 13/412,122.
Final Office Action dated Jul. 25, 2013 from corresponding U.S. Appl. No. 13/412,122.
Notice of Allowance dated Sep. 13, 2013 from corresponding U.S. Appl. No. 13/412,122.
Communication from European Examining Division dated Oct. 23, 2006 from corresponding European Patent Application No. 03706179.3.
Alpendurada., "Solid-phase Microextraction: a Promising Technique for Sample Preparation in Environmental Analysis," Journal of Chromatography. A, Aug. 2000, vol. 889 (1-2), pp. 3-14.
Hu et al., "Solid-phase Microextraction of Phenol Compounds Using a Fused-silica Fiber Coated With Beta-cyclodextrin-bonded Silica Particles," Analytical Sciences, Apr. 2004, vol. 20 (4), pp. 667-671.
International Patent Application No. PCT/CA2015/050551, International Preliminary Report on Patentability dated Dec. 22, 2016.
International Patent Application No. PCT/CA2003/000311, International Search Report dated Oct. 10, 2001.
Kataoka et al., "Applications of Solid-Phase Microextraction in Food Analysis," Journal of Chromatography A, Jun. 2000, vol. 880 (1-2), pp. 35-62.
Louch et al., "Dynamics of Organic Compound Extraction from Water Using Liquid-Coated Fused Silica Fibers," Analytical Chemistry, May 1992, vol. 64 (10), pp. 1187-1199.
Martos et al., "Calibration of Solid Phase Microextraction for Air Analyses Based on Physical Chemical Properties of the Coating," Analytical Chemistry, Jan. 1997, vol. 69 (2), pp. 206-215.
Vail et al., "Rapid and Unambiguous Identification of Melamine in Contaminated Pet Food Based on Mass Spectrometry with Four Degrees of Confirmation", Journal of Analytical Toxicology, Jul./Aug. 2007, vol. 31 (6), pp. 304-312.
Poerschmann et al., "Solid Phase Microextraction for Determining the Distribution of Chemicals in Aqueous Matrices", Journal of Analytical Chemistry, Feb. 1997, vol. 69 (4), pp. 597-600.

(56) References Cited

OTHER PUBLICATIONS

Reubsaet et al., "Determination of Benzodiazepines in Human Urine and Plasma with Solvent Modified Solid Phase Micro Extraction and Gas Chromatography; Rationalisation of Method Development Using Experimental Design Strategies," Journal of Pharmaceutical and Biomedical Analysis, Dec. 1998, vol. 18 (4-5), pp. 667-680.

U.S. Appl. No. 14/705,238, Non-Final Office Action dated Sep. 7, 2016.

U.S. Appl. No. 14/738,688, Office Action dated Nov. 10, 2016.

U.S. Appl. No. 14/738,678, Non-Final Office Action dated Mar. 22, 2017.

International Patent Application No. PCT/CA2015/050550, International Preliminary Report on Patentability dated Dec. 22, 2016.

Mirnaghi et al., "Reusable Solid-Phase Microextraction Coating for Direct Immersion whole-Blood Analysis and Extracted Blood Spot Sampling Coupled with Liquid Chromatograpy—Tandem Mass Sepctrometry and Direct Analysis in Real Time—Tandem Mass Spectrometry", Analytical Chemistry, Aug. 2012, vol. 84 (19), pp. 8301-8309.

U.S. Appl. No. 14/705,238, Restriction Requirement dated May 19, 2016.

Chipuk et al., "The Influence of Material and Mesh Characteristics on Transmission Mode Desorption Electrospray Ionization," Journal of the American Society for Mass Spectrometry, Apr. 2009, vol. 20 (4), pp. 584-592.

Chipuk et al., "Transmission Mode Desorption Electrospray Ionization," Journal of the American Society for Mass Spectrometry, Nov. 2008, vol. 19 (11), pp. 1612-1620.

Gomez-Rios et al., "Solid Phase Microextraction (SPME)-Transmission Mode (TM) Pushes Down Detection Limits in Direct Analysis in Real Time (DART);" Chemical Communications, Aug. 2014, vol. 50, pp. 12937-12940.

Mirnaghi et al., "Optimization of the Coating Procedure for a High-Throughput 96-Blade Solid Phase Microextraction System Coupled with LC-MS/MS for Analysis of Complex Samples," Analytical Chemistry, Jun. 2011, vol. 83 (15), pp. 6018-6025.

Perez et al., "Transmission-Mode Direct Analysis in Real Time and Desorption Electrospray Ionization Mass Spectrometry of Insecticide-Treated Bednets for Malaria Control," Analyst, Feb. 2010, vol. 135, pp. 712-719.

Rodriguez-Lafuente et al., "Determination of Cocaine and Methadone in Urine Samples by Thin-Film Solid-Phase Microextraction and Direct Analysis in Real Time (DART) Coupled With Tandem Mass Spectrometry," Analytical and Bioanalytical Chemistry, Dec. 2013, vol. 405 (30), pp. 9723-9727.

\* cited by examiner

Fig. 3

METHOD FOR MEASURING OR IDENTIFYING A COMPONENT OF INTEREST IN A BIOLOGICAL SYSTEM

CROSS-REFERENCE TO RELATED APPLICATIONS

This application is a continuation of U.S. patent application Ser. No. 14/492,411, filed on Sep. 22, 2014; which was a divisional application of U.S. patent application Ser. No. 13/478,295, filed on May 23, 2012; which was a divisional of U.S. patent application Ser. No. 12/174,494, filed Jul. 16, 2008; which was a continuation-in-part of U.S. patent application Ser. No. 11/706,167, filed Feb. 15, 2007 (now U.S. Pat. No. 8,008,064), which is a continuation of U.S. patent application Ser. No. 11/208,933 filed Aug. 23, 2005 (now U.S. Pat. No. 7,232,689), which is a continuation-in-part of U.S. patent application Ser. No. 10/506,827 filed Sep. 7, 2004 (now U.S. Pat. No. 7,384,794) which is derived from International Patent Application PCT/CA2003/0000311, which claims benefit of U.S. Patent Application 60/364,214 filed Mar. 11, 2002; U.S. Patent Application 60/393,309 filed Jul. 3, 2002; U.S. Patent Application 60/421,001 filed Oct. 25, 2002; U.S. Patent Application 60/421,510 filed Oct. 28, 2002; and U.S. Patent Application 60/427,833 filed Nov. 21, 2002. The entirety of each document being incorporated herein by reference.

FIELD

The present disclosure relates to the extraction of small molecules of interest from a matrix, and in particular, to methods of preparation and use of biocompatible coatings and coated devices for sampling devices used for extracting components of interest in a biological matrix for further quantification or identification.

BACKGROUND

Presently, if one wants to accurately assess the concentrations of chemicals or drugs inside a living animal, a sample of the blood or tissue to be studied is removed from the animal and taken to an analytical laboratory to have the chemicals of interest extracted and quantified. Typically, a first step is a pre-treatment of the sample to convert it to a form more suitable for chemical extraction. In the case of blood, this may be by the removal of blood cells and/or some blood components by the preparation of serum or plasma. In the case of a tissue sample, this may be by many processes, including: freezing, grinding, homogenizing, enzyme treatment (e.g., protease or cellulase) or hydrolysis. Subsequently, compounds of interest are extracted and concentrated from the processed sample. For example serum samples may be subjected to liquid-liquid extraction, solid phase extraction or protein precipitation, followed by drying and reconstitution in an injection solvent. A portion of the injection solvent is introduced to an analytical instrument for chromatographic separation and quantification of the components. This method produces accurate results with high specificity for the compound of interest, but is time consuming and labor intensive. Also, because of the large number of steps in the process there is a significant chance of errors in sample preparation impacting the results. This method has good sensitivity and selectivity and accuracy for the target compounds but is limited in that the chemical balance inside the animal is disrupted during sampling. In many cases, this disruption reduces the value of the results obtained, and in some cases makes this technique inappropriate for the analysis. Where the removed blood volume is a high proportion of the total blood volume of the animal, as is commonly the case when mice are used, the death of the animal results. This means that a different animal must be used for each data point and each repeat By eliminating the need for a blood draw in this case, fewer animals would be required for testing and a significant improvement in inter-animal variation in the results would be achieved.

Alternatively, biosensors have been developed for some applications of analysis of chemical concentrations inside animals. In this case, a device consisting of a specific sensing element with an associated transducer is implanted. The device produces a signal collected by an electronic data logger that is proportional to the chemicals to which the sensor responds. The main limitations of this type of device are that they normally respond to a spectrum of chemicals rather than having specificity for only one chemical. Of the spectrum of chemicals to which the sensor responds, some produce a greater and some a lesser response. Sensors are also susceptible to interferences where another chemical present in a system interferes with the response produced by the target chemicals. It is for these reasons that biosensors are normally limited in terms of accuracy and precision. Additionally, biosensors are typically not as sensitive to low chemical concentrations as state-of-the-art, stand-alone, detectors. Such detectors, for example mass spectrometers, are used in the above mentioned conventional analysis techniques and in solid phase microextraction.

Microextraction is a significant departure from conventional 'sampling' techniques, where a portion of the system under study is removed from its natural environment and the compounds of interest extracted and analyzed in a laboratory environment. As with any microextraction, compounds of interest are not exhaustively removed from the investigated system, and conditions can be devised where only a small proportion of the total amount of compound, and none of the matrix, are removed. This avoids disturbing the normal balance of chemical components. This could have a benefit in the non-destructive analysis of very small tissue sites or samples. Because extracted chemicals can be separated chromatographically and quantified by highly sensitive analytical instruments, high accuracy, sensitivity and selectivity are achieved.

With current commercially available solid phase microextraction (SPME) devices, a stationary extraction phase is coated onto a fused silica fiber. The coated portion of the fiber is typically about 1 cm long and coatings have various thicknesses. The fiber can be mounted into a stainless steel support tube and housed in a syringe-like device for ease of use. Extractions are performed by exposing the extraction phase to a sample for a we-determined time to allow sample components to come into equilibrium with the extraction phase. After extraction, the fiber is removed to an analytical instrument (typically a gas or liquid chromatograph) where extracted components are desorbed and analysed. The amount of a component extracted is proportional to its concentration in the sample (J. Pawliszyn "Method and Device for Solid Phase Microextraction and Desorption", U.S. Pat. No. 5,691,206).

To date, commercial SPME devices have been used in some applications of direct analysis of living systems. For example they have been applied for the analysis of airborne pheromones and semiochemieals used in chemical communications by insects (Moneti, Dani, F. R.; Pieraccini, G. T. S. Rapid Commun. Mass Spectrom. 1997, 11, 857-862), (Frerot, B.; Malosse, C.; Cain, A. H. J. High Resolut. Chromatogr, 1997, 20, 340-342) and frogs (Smith, B. P.; Zini, C. A.; Pawliszyn, J.; Tyler, M. J.; Hayasaka, Y.; Williams, B.; Caramao, E. R. Chemistry and Ecology 2000, 17, 215-225) respectively. In these cases, the living animals were non-invasively monitored over time by assessing the chemical concentrations in the air around the animal, providing a convenient means to study complicated dynamic processes without interference.

The current commercial devices do, however, have some limitations for in vivo and in vitro analysis of a biological matrix, such as blood or tissue. Firstly, the most difficult and undesirable problem is the adsorption of proteins and other macromolecules on the surface of SPME fibers. Macromolecules are understood to be biological components with a molecular mass greater than about 10,000 atomic mass units. These macromolecules constitute a diffusion barrier and decrease the extraction efficiency in subsequent experiments. In order to transfer all SPME advantages to the field of in vivo and in vitro analysis of biological samples, it is imperative to develop new biocompatible devices suitable for extracting compounds from biological matrices.

Devices can be made biocompatible by coating them with a biocompatible material. Custom-made coatings based on polypyrrole (PPY) (Lord, H. L.; Grant, R. P.; Walles, M.; Incledon, B.; Fahie, B.; Pawliszyn, J. B., Anal. Chem. 2003, 75(19), 5103-5115) and poly(ethylene glycol) (PEG) (Musteata, F. M.; Musteata, M. L; Pawliszyn, J., Clin Chem 2006, 52(4), 708-715) have been used for in vivo drug analysis. Other biocompatible materials include restricted access materials (RAM, ionic liquids (IL), polydimethylsiloxane (PDMS), polypyrrole, and polyethylene glycol). Biocompatible membranes have also been prepared from polyacrylonitrile (Nie, F.-Q.; Xu, Z.-K.; Ming, Y.-Q.; Kou, R.-Q.; Liu, Z.-M.; Wang, S.-Y. Desalination 2004, 160, 43-50. Lavaud, S.; Canivet, E.; Wuillai, A.; Maheut, H.; Randoux, C.; Bonnet, J.-M.; Renaux, J.-L.; Chanard, J. Nephrology, Dialysis, Transplantation 2003, 18, 2097-2104. Yang, M. C.; Lin, W. C. Journal of Polymer Research 2002, 9, 201-206), polyurethane, chitosan, and cellulose.

Polymers such as polypyrroles, derivatised cellulose, polysulfones, polyacrylonitrile (PAN), polyethylene glycol and polyamides are currently used to prepare biocompatible membranes used for separation of sub-micron particles in biomedical applications. PAN has been widely used as membrane material in the fields of dialysis and ultrafiltration. It has been found that its properties can be fine-tuned by using specific co-monomers. The terms "polyacrylonitrile" and "PAN" are used herein to refer to homopolymers as well as copolymers of acrylonitirile containing at least about 85% by weight acrylonitrile and up to about 15% by weight of at least one other ethylenically unsaturated compound copolymerizable with acrylonitrile. For example, PAN can be tailored with a reactive group for enzyme immobilization. Furthermore, some co-monomers lead to improved mechanical strength, solvent resistance, high permeation flux, and biocompatibility. Accordingly, PAN-based membranes have great potential for the treatment of wastewater, the production of ultra-pure water, hemodialysis artificial kidneys, and biocatalysis with separation. PAN is one of the most important polymers used in the biomedical area because of its exceptional qualities, such as good thermal, chemical, and mechanical stability as well as biocompatibility. Membranes made of PAN are widely used as dialyzers able to remove low to middle molecular weight proteins and for high-flux dialysis therapy. PAN is one of the best polymers in terms of biocompatibility.

However, good extractive materials are generally not biocompatible and PAN is not appropriate as an extractive material for SPME.

It is, therefore, desirable to provide a biocompatible composition able to extract small molecules from a matrix for use with solid phase microextraction devices, as well as a process for coating SPME fibers with said composition.

SUMMARY

The inventors of the present disclosure conceived of a method to obviate or mitigate at least one disadvantage of previous biocompatible compositions for solid phase microextraction devices.

According to one aspect, a process for coating a fiber with a biocompatible coating for use of the fiber in solid phase microextraction (SPME) of a small molecule of interest from a matrix. The process includes the step of coating the fiber with a coating of a biocompatible polymer and a solvent having solid phase microextraction (SPME) particles with pores dimensioned to absorb the small molecule of interest from the matrix suspended therein. The process also includes the steps of drying the coated fiber to remove the solvent and curing the dried coated fiber at an elevated temperature.

According to another aspect, a process for preparing a device for use in solid phase microextraction (SPME) of a small molecule of interest from a biological matrix. The process includes identifying the small molecule of interest to be extracted from the matrix and selecting extraction phase SPME particles having pores dimensioned to absorb the identified small molecule of interest from the matrix. The process also includes the process step of selecting a biocompatible polymer for suspending the SPME particles wherein the selection of the biocompatible polymer being responsive to the biocompatible polymers characteristic to reduce the adsorption of proteins and macromolecules onto the suspended SPME particles while allowing the SPME particles to extract the small molecule of interest from the matrix. The process further includes the steps of selecting a solvent for combining with the selected biocompatible polymer, dissolving the selected biocompatible polymer in the selected solvent and combining the selected SPME particles with the combination of the dissolved biocompatible polymer and the solvent to form a solid phase microextraction (SPME) coating solution.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments will now be described, by way of example only, with reference to the attached Figures, wherein.

DETAILED DESCRIPTION

One embodiment relates to coatings which can be used for direct microextraction of small molecules from a biological matrix, such as fluids or tissues. The biological fluids can be whole blood, serum, plasma, cerebrospinal fluid, peritoneal fluid, saliva or urine. The tissue could be, for example, isolated cells or organs. The small molecules can be drugs. The small molecules can be hydrophobic or hydrophilic and should generally weigh less than 10,000 atomic mass units. The small molecules can be drugs or biomarkers. A biomarker is a physiological substance that when present in abnormal amounts may indicate the presence of disease. The coatings can be prepared by covering flexible fibers with a suspension of various extractive particles (for example: C-18/silica, RP-amide/silica, or HS-F5/silica) in a polyacrylonitrile (PAN), polyethylene glycol, polypyrrole, derivatised cellulose, polysulfone, or polyamide solution. C-18/silica particles would be understood by one of skill in the art to comprise silica particles derivatized with a hydrophobic phase, the hydrophobic bonded phase comprising octadecyl. For RP-amide-silica particles, the bonded phase comprises palmitamido-propyl. For HS-F5-silica particles, the bonded phase comprises pentafluorophenyl-propyl. The particles can be about 17 to about 50 μm particles. Preferably, the particles can be about 2 to about 20 μm particles. Preferably, the particles can be about 3 to about 10 μm particles. More preferably, the particles can be about 3 to about 7 μm particles. The particles can be spherical. The pore size diameter can be about 10 to about 200 Å. Preferably, the pore size can be about 100 to about 180. The surface area can be about 200 $m^2/g$ to about 800 $m^2/g$. Preferably, the surface area can be about 200 $m^2/g$ to about 300 $m^2/g$.

It would be understood by a person of skill in the art that appropriate coatings can be formed with other extractive particles, and particularly with any extractive particles currently used in solid phase extraction or affinity chromatography (e.g. high pressure liquid chromatography), depending, on the nature of the compound being extracted, in a similar manner than affinity chromatography relies on different particles for separating various compounds. For example, other particles could include such particles as: normal-phase silica, C1/silica, C4/silica, C6/silica, C8/silica, C30/silica, phenyl/silica, cyano/silica, diol/silica, ionic liquid/silica, molecular imprinted polymer particles, carboxen 1006 or divinylbenzene. Mixtures of particles can also be used in the coatings. The particles can be inorganic (e.g. silica), organic (e.g. carboxen or divinylbenzene) or inorganic/organic hybrid (e.g. silica and organic polymer), Furthermore, a person of skill in the art would understand that other biocompatible polymers could be used as glue or support. PAN can also be used for covering existing commercial extraction phases for example: carbowax/templated resin) with a biocompatible layer.

It would be readily understood by one of skill in the art that the diameter of a fiber for SPME can be of millimeter to nanometer dimensions. Preferably, the diameter of a fiber can be between 0.1 millimeters and 0.6 millimeters, More preferably, the diameter of a fiber can be about 0.13 millimeters (0.005 inches), The wire can be formed of any acceptable material that would be amenable for use in a biological matrix. Such material may include silica, plastic, carbon or metal wire. Metal wires may be stainless steel, titanium, a nickel-titanium alloy, or any other metal wire known to a person of skill in the art. The flexible, inert, biocompatible nickel-titanium alloy can be Nitinol, A metal with shape memory properties that enable the wire to maintain straightness, even after it is coiled, can be desirable.

Coated SPME wires can be used for in vitro analysis of drug concentrations as well as for in vivo analysis of intravenous drug concentrations in a living animal, Coated SPME, probes for in vivo analysis can have any combination of extractive particles coated with an appropriate biocompatible coating, such as polyacrylonitrile (PAN), polyethylene glycol, polypyrrole, derivatised cellulose, polysulfone, or polyimide solution, Non-limiting examples of the coating include: a PAN/C-18 coating, a PAN/RP-amide coating, a polyethylene glycol/HSF5 coating, a derivatised cellulose/C-18 coating, a polypyrrole/C-30 coating, a polysulfone/phenyl coating and polyamide/cyano coating.

Another embodiment relates to a continuous-coating process for producing SPME fibers coated with a biocompatible coating. Preferably, the biocompatible coating is PAN or Polyethylene glycol (PEG). In the continuous-coating process, a fiber can be wound on a spool and can be threaded through an applicator with a fixed opening that contains a suspension of extraction particles in a biocompatible coating solution. The extraction particles can be C-18, RP-amide, HS-F5 silica particles or any other particle listed above, Mixtures of particles can be used. When the particles are silica particles and the biocompatible coating is RAN, the ratio of PAN/silica can be between 0.3 and 0.7 wt/wt. The preferred ratio of PAN/silica is 0.5 wt/wt. The ratio is based on the bare weight of silica and adjusted to the phase loading on the silica particles. The PAN/solvent solution can be between 5% and 15% PAN (w/w), Preferably, the PAN/solvent solution is between about 7.5% and about 12% PAN (w/w). More preferably, the PAN/solvent solution is about 10% PAN/solvent (w/w). The solvent can be any solvent known to one of skill in the art that dissolves PAN, for example: dimethylformamide (DMF), dimethyl sulfoxide, NaSCN, $Ca(CNS)_2$, nitric acid, ethylene carbonate or mixtures thereof, More preferably, the solvent can be DMF. The suspension can be coated on a length of flexible metal fiber. The coated fiber can be passed through a heater at an elevated temperature and connected to another reel driven by a motor that can pull the fiber at a fixed speed. The elevated temperature can be between about 150° C. and about 300° C. Preferably, the elevated temperature is between about 180° C. and about 210° C. A person of skill in the art would readily understand that PAN is fully polymerized when it is dissolved in the solvent and as long as the solvent is fully evaporated, the fiber is properly coated. As such, any means known to a person of skill in the art to remove the solvent can be used to dry the coated fibers.

In the continuous-coating process, thin multiple layers of the suspension can be applied to the fiber until the desired coating thickness is obtained. The advantage is that each coating layer is bonded and the coating thickness is uniform throughout the length of the fiber. When the process parameters are controlled by automation, reproducibility between fibers can be greatly improved.

Another embodiment relates to a dip-coating process for p producing SPME fibers coated with a biocompatible coating. Preferably, the biocompatible coating is PAN. A dip-coating process would be understood by a person of skill in the art to be a batch process. A length of fiber can be dipped into a suspension of extraction particles in a biocompatible coating solution. The extraction particles can be C-18, RP-amide, HS-F5 silica particles or any other particle listed above. Mixtures of particles can be used. When the particles are silica particles and the biocompatible coating is PAN, the ratio of PAN/silica can be between 0.3 and 0.7 wt/wt. The preferred ratio of PAN/silica is 0.5 wt/wt. The ratio is based on the bare weight of silica and adjusted to the phase loading on the silica particles. The PAN/solvent solution can be between about 5% and about 15% PAN (w/w). Preferably, the PAN/solvent solution can be between about 7.5% and 12% PAN (w/w). More preferably, the PAN/solvent solution can be about 10% PAN/solvent w/w. The solvent can be dimethylformamide (DMF), dimethyl sulfoxide, NaSCN. $Ca(CNS)_2$, nitric acid, ethylene carbonate or mixtures thereof. More preferably, the solvent can be DMF.

If desired, the coated fibers can be dried under flowing nitrogen and then cured for about 5 s to about 1.5 min at about 180° C. to about 200° C. in order to accelerate the removal of the solvent. A person of skill in the art would readily understand that PAN is fully polymerized when it is dissolved in the solvent and as long as the solvent is fully evaporated, the fiber is properly coated. As such, any means known to a person of skill in the art to remove the solvent can be used to dry the coated fibers.

The wires can be pre-processed before the coating process in order to clean and roughen the surface. Pre-processing can be accomplished by washing with acetone, etching for 1 min in concentrated hydrochloric acid, washing the wire with water and/or thoroughly cleaning the wire by sonication in water. Prior to use, the coated fibers can be conditioned in a water:methanol 50:50 wash for 30 min. Conditioning the C-18 based coatings with water or higher proportion of methanol can lead to worse reproducibility. Other coatings, however, can require only a very brief conditioning step (less than 5 min), or even none at all.

Example 1—Dip Coating

Particles commonly used as HPLC stationary phases (0.47 g of C-18, RP-amide, or HS-F5 particles) were brought into suspension with 2 g of a solution made up of 10% w/w PAN in DMF. SPME coatings with a length of 1.5 cm were prepared by applying a uniform layer of slurry of PAN and different particles on the surface of stainless steel wires, allowing to dry under flowing nitrogen, and finally curing for about 1.5 min at 180° C. The SPME coating was applied by dipping the wires into the slurry and removing them slowly.

Example 2—PAN as a Membrane

Existing fibers with conventional extraction phases (CW/TPR-carbowax/templated resin, from Supelco, Pa.) were coated with PAN by dipping them for 2 min in a solution of 10% PAN in DMF. Subsequently, the fibers were removed slowly from the solution, allowed to dry under flowing nitrogen, and finally cured by a short exposure (5 s) to a flow of nitrogen at 200° C.

Example 3—Continuous Coating

Wire was coiled on a first reel and threaded through an applicator filled with a coating suspension. The wire was then threaded through a heater and attached to a take-up reel. The wire was drawn through the both the applicator and heater at a set speed. The thickness of the coating was measured and additional coatings were applied by switching the positions of the first reel and take-up reel, and repeating the previous coating, drying and switching steps until a desired thickness is achieved.

Example 4—Analysis by Scanning Electron Microscopy

Figure 1A:
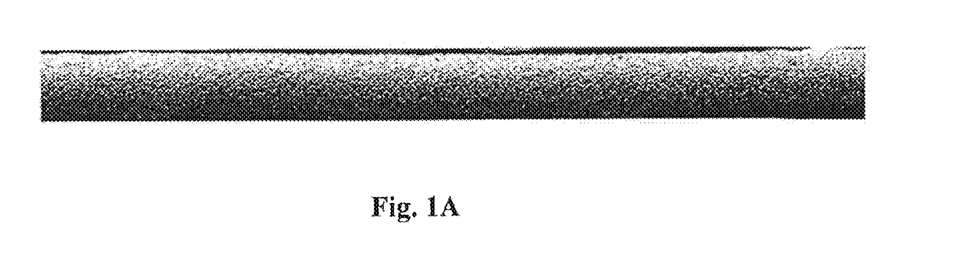
FIG. 1A shows a scanning electron micrograph image, at 100× magnification, of a fiber coated with a coating of an exemplary embodiment.
Figure 1B:
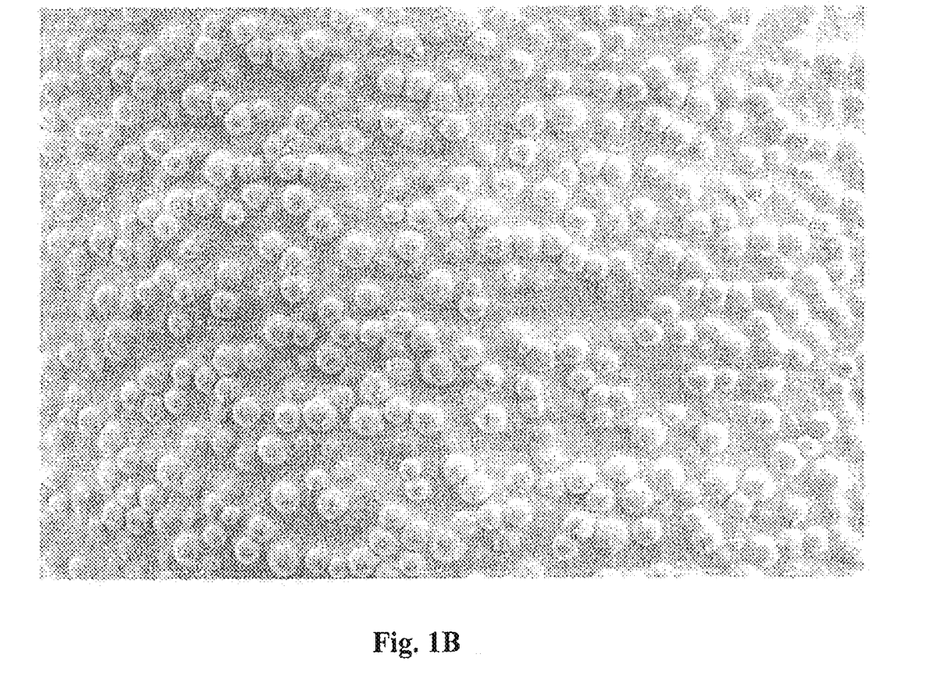
FIG. 1B shows the scanning electron micrograph image at 1000× magnification.

For SEM imaging, the fibers were cut into 7 mm long pieces, coated with gold (~10 nm) and analyzed using a LEO 1530 Emission Scanning Electron Microscope at the Waterloo Watlab Facility. The SEM images of PAN/C-18 coatings (FIG. 1) demonstrate that the particles are completely covered with PAN and are homogeneously distributed within the coating.

SEM was also used to estimate the average thickness of each coating, which was found to be 60-62 µm, No swelling of the coating was observed during analysis time (extraction up to about 2 h and desorption for about 15 min).

Example 5—Analysis by X-Ray Photoelectron Spectroscopy

XPS (X-ray photoelectron spectroscopy) analyses were performed by using a multi-technique ultra-high vacuum. Imaging XPS Microprobe system (Thermo VG Scientific ESCALab 250) equipped with a hemispherical analyzer with a mean radius of 150 mm and a monochromatic. Al-K$\alpha$ (1486.60 eV) X-ray source. The spot size for the XPS analysis used for the present work was approximately 0.5 mm by 1.0 mm. The samples were mounted on a stainless steel sample holder with double-sided carbon tapes. The sample was stored in vacuum ($2\times10^{-8}$ mbar) in the load-lock chamber of the Imaging XPS Microprobe system overnight to remove any remaining moisture before introduction into the analysis chamber maintained at $2\times10^{-10}$ mbar. A combination of low energy electrons and ions was used for charge compensation on the non-conducting coating material during the analysis conducted at room temperature. Averages of five high resolution XPS scans were performed for each element of interest (C, N, O, S). Curve fitting was performed using CasaXPS VAMAS Processing Software and the binding energies of individual elements were identified with reference to the NIST X-Ray Photoelectron Spectroscopy Database.

All investigated fibers were exposed to undiluted human plasma at 37° C., for 1 h (this is considered a rigorous biocompatibility test). They were then briefly washed with phosphate buffer and deionized water and dried in nitrogen before analysis. Survey scans and high resolution XPS scans were used to determine the atomic percentages of the surfaces before and after exposure to plasma, as described in Example 8, Example 6—Analysis by LC/MS Stock solutions of drugs (diazepam, verapamil, warfarin, nordiazepam, loperamide, and lorazepam as internal standard) with a concentration of 1 mM were prepared in a water:methanol 1:1 mixture and kept refrigerated at 4° C. (in 2 mL silanized vials).

Human plasma (in 2 mL polypropylene vials with EDTA as anti-clotting agent) was stored at −20° C. until analysis. For analysis, plasma was thawed at room temperature and aliquots of 1.5 mL plasma were transferred into clean vials. Appropriate amounts of stock drug solution were added to obtain final concentrations of drug in the range 1 nM-50 µM, followed by vortex mixing for 1 minute. Samples and standards in PBS (phosphate buffer saline) were similarly prepared, to a final concentration in the range 0.1 nM-5 µM.

The time required for the drugs to reach equilibrium between the sample and the SPME fiber, for plasma and PBS samples at 2400 rpm vortex stirring and room temperature, was determined for all target compounds (diazepam, verapamil, and nordiazepam 5E-7M; warfarin 5E-6M; loperamide 5E-8M) by measuring the amount of compound extracted at different time points. Although the concentration of the sample analyzed by SPME has no impact on the extraction time profile and equilibration time, the agitation conditions, coating thickness (especially for liquid coatings), distribution constant, and diffusion coefficient of the analyte play very important roles in determining an experimental equilibration time. While the theoretical equilibration time is infinite, the experimental equilibration time can be considered to be the time required to extract at least 95% of the theoretical maximum.

To minimize the errors caused by different sampling times, the extraction time should be equal to or longer than the experimental equilibrium time. The experimentally determined equilibration time was found to be between 4 and 55 min in most cases. No significant difference was observed when the equilibration profile in PBS was compared to the equilibration profile in plasma. When the target drugs were analyzed in mixtures, an extraction time corresponding to the maximum equilibration time was used.

Figure 2:
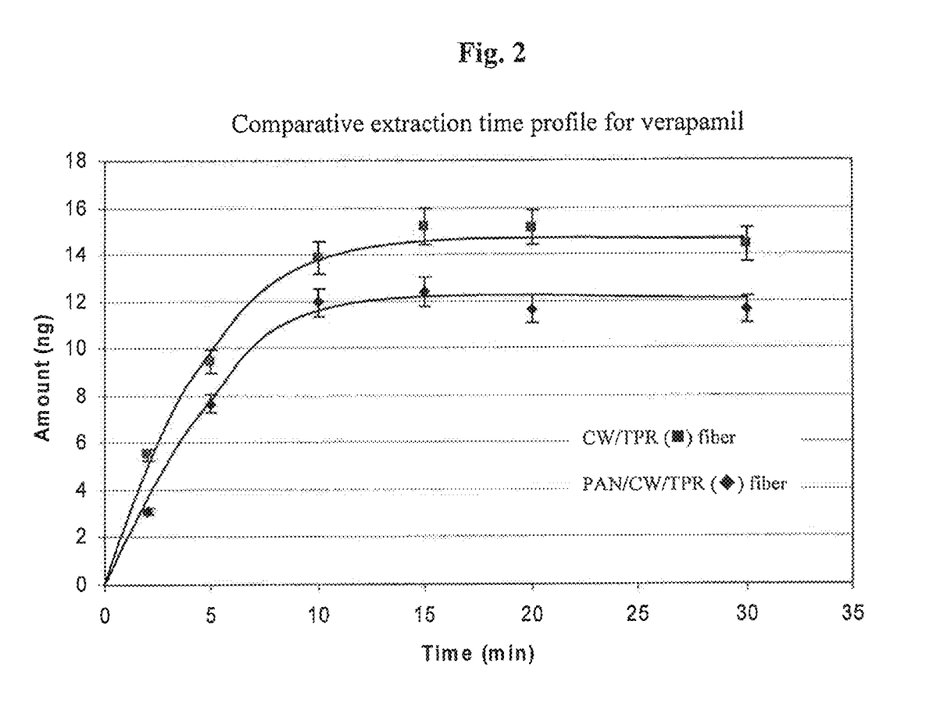
FIG. 2 shows comparative extraction profiles over time for non-coated SPME fibers and SPME fibers that are coated with a biocompatible coating.

When existing commercial coatings were covered with a layer of PAN, the equilibration time remained essentially unchanged. The mechanical stability of the fibers coated with PAN can be significantly improved: while original fibers can be used for 20 extractions before they break down, those coated with PAN can last for more than 50 extractions, in addition to improved biocompatibility and durability, the PAN coated fibers offer almost the same extraction capacity as the non-coated fibers (FIG. 2).

For extraction, samples were placed on a digital vortex platform and the extracting phase of the SPME fiber was immersed in the sample for a precise period of time, as determined above. Subsequently, the fiber was then briefly rinsed with water, and desorbed for analysis. The lowest carryover and the sharpest chromatographic peaks for the investigated drugs were obtained for a desorption time of 15 min, vortex stirring at 2400 rpm, and with a desorption solution prepared from acetonitrile:water:acetic acid (50:49:1). Unless otherwise specified, the sample volume was 1.5 mL and the fiber was desorbed for 15 minutes in an insert with 60 µL desorption solution containing lorazepam as internal standard (50 ng/mL).

Successful coupling of SPME with HPLC is dependent on the efficiency of the desorption step. Desorption can be effected on-line (manual introduction of the fiber into a desorption chamber) or off-line (in a vial or 96-well plate).

The carryover was found to be well below 3% (with three exceptions out of twenty determinations). For highly sensitive analyses, desorption is usually followed by solvent evaporation and reconstitution in a lower volume of solvent suitable for direct HPLC analysis. Nevertheless, desorption in 60 µL solvent was found to be entirely suitable. If required, the carryover can be further decreased by using larger volumes of desorption solution or longer desorption time.

All reproducibility, reusability, extraction efficiency, and calibration experiments were performed at equilibrium in similar conditions, following the general procedure for new SPME methods. Calibration curves were constructed by spiking PBS or human plasma with drug concentrations in the range of 0.5 nM-50 µM, which generally covers the therapeutic concentrations. All extractions and desorptions were performed manually.

LC-MS (liquid chromatography coupled with mass spectrometry) analyses were performed using an Agilent 1100 series liquid chromatograph (Agilent Technologies, Palo Alto, Calif.), equipped with a vacuum solvent degassing unit, a binary high pressure gradient pump, an autosampler, a column thermostat and a variable wavelength UV-VIS detector coupled on-line with an Agilent 1100 series MSD single quadrupole instrument with atmospheric pressure electrospray-ionization (ESI). High purity nitrogen used as nebulizing and drying gas was obtained from an in-house generator.

Chromatographic separations were carried out on a Discovery® C18 column (5 cm×2.1 mm, 5 µm particles, from Supelco), guarded by an on-line filter (0.2 µm), Data were collected and analyzed using the CHEMSTATION software from Agilent Technologies.

LC and ESI-MS conditions were as follows: column temperature 25° C., mobile phase acetonitrile: 20 mM ammonium acetate pH=7.0 with gradient programming (initial composition—10:90, ramped to 80:20 over 6 min and maintained until the end of the run), flow rate 0.25 mL min$^{-1}$, nebulizer gas $N_2$ (35 psi), drying gas $N_2$ (13 L min$^{-1}$, 300° C.), capillary voltage 3500 V, fragmentor voltage 80 V, quadrupole temperature 100° C., positive ionization mode, Total run time was 9 min.

For optimization experiments, scan mode in the range 100-1500 amu was used; for quantification experiments, selected ion monitoring is used, with a scan time of 0.42 s/cycle and a dwell time of 65 ms. The following positive ions were monitored: diazepam, m/z 285.1; verapamil, m/z 455.3; warfarin, m/z 309.1; nordiazepam, m/z 271.1; loperamide, m/z 477.3; lorazepam, m/z 321.0. All other parameters of the mass-selective detector were automatically optimized using a calibration standard. Lorazepam was used as an internal standard for compensation of variations in the injection volume (20 µL).

Example 7—Sterilization

Sterilization may be desired if the microextraction devices are to be used for in vivo experiments. Current sterilization methods include heat, steam, chemical (ethylene oxide, alcohols, aldehydes), and radiation.

The new coatings were tested for extraction efficiency before and after chemical and steam sterilization. For chemical sterilization, the fibers were immersed in alcohol (methanol or ethanol) for 30 minutes and then allowed to dry. Sterilization by steam was performed in an autoclave at 121° C. and 15 psi for 30 minutes.

No change in extraction efficiency was observed upon sterilization with alcohols, as this step is similar to the conditioning step (before extraction). In the case of sterilization in an autoclave, the proposed coatings showed no sign of deterioration (as determined from optical microscope images). This was expected since PAN coatings are known to withstand (2C-injector temperatures (>250° C.). Although no signs of breakdown were observed, the extraction capacity decreased by approximately 15% after sterilization, possibly because of the combined effect of heat and water vapors on the fused silica particles.

Example 8—Biocompatibility

Many methods have been applied for the study of biocompatibility, ranging from the simple visual inspection to the most sensitive atomic force microscopes. Nevertheless, only a few methods are widely used and recognized: XPS, atomic force microscopy, surface plasmon resonance, and competitive ELISA (enzyme linked immunosorbant assay).

XPS or electron spectroscopy for chemical analysis (ESCA) is one of the most common types of spectroscopic methods for analysis of surfaces. The sampling depth for this method is approximately 1-30 nm (up to 100 nm mean-free pass), which encompasses a surface region highly relevant for bio-interactions.

The biocompatibility of various coatings was tested by XPS. A material is considered biocompatible if the amount of nitrogen and sulfur on the surface does not increase significantly after contact with a biological system. After exposure of PAN-based coatings to plasma, the amount of nitrogen and carbon on the surface generally decreases, accompanied by an increase in the amount of oxygen (Table 1). These observations suggest that most of the molecules adsorbed from human plasma contain a high percent of oxygen (usually because of non-specific adsorption), while their nitrogen content is lower than that of plasma proteins. Even more conclusive from a biocompatibility point of view is the amount of sulfur on the surface, since sulfur is naturally present in proteins but absent from the investigated SPME coatings. When compared to RAM and PPY, materials regarded as highly biocompatible, the new coatings based on PAN showed a much lower increase in sulfur.

TABLE 1

Atomic composition obtained by XPS for selected proteins and coatings (before and after exposure to human plasma); hydrogen is not reported, as it is not detectable by XPS.

| Protein/Coating | C % (RSD < 5%) | N % (RSD < 5%) | O % (RSD < 10%) | S % (RSD < 15%) |
|---|---|---|---|---|
| Human serum albumin | 63.3 | 16.9 | 19.0 | 0.9 |
| Fibrinogen | 62.8 | 18.0 | 18.8 | 0.5 |
| PAN coating (bp*) | 78.2 | 17.6 | 4.0 | 0.0 |
| PAN coating (ap**) | 73.5 | 15.1 | 11.3 | 0.0 |
| PAN/C-18 (bp*) | 77.0 | 17.2 | 5.7 | 0.0 |
| PAN/C-18 (ap**) | 73.6 | 13.9 | 12.5 | 0.0§ |
| PAN/RP-amide (bp*) | 78.3 | 17.0 | 4.5 | 0.0 |
| PAN/RP-amide (ap**) | 68.6 | 15.5 | 15.8 | 0.0 |
| PAN/HS-F5 (bp*) | 79.3 | 20.1 | 0.4 | 0.0 |
| PAN/HS-F5 (ap**) | 70.9 | 15.2 | 13.7 | 0.0 |
| PAN/RAM (bp*) | 78.9 | 20.4 | 0.5 | 0.0 |
| PAN/RAM (ap**) | 72.6 | 16.3 | 10.4 | 0.5 |
| PPY (bp*) | 61.0 | 3.8 | 35.2 | 0.0 |
| PPY (ap**) | 69.7 | 12.4 | 17.6 | 0.3 |

*bp = before exposure to human plasma
**ap = after exposure to human plasma
§the experimental value was 0.04, below the limit of quantitation of 0.1%

The biocompatibility test based on XPS suggests that the most biocompatible PAN-based coatings are PAN/RP-amide and PAN/HS-F5, followed closely by PAN/C-18, Furthermore, the newly developed PAN-based coatings were inspected under the microscope after five minutes exposure to human plasma and whole mouse blood (without anti-clotting agents), and no clot adhesion to the coating was observed.

Example 9—Drug-Plasma Protein Binding

Figure 3:
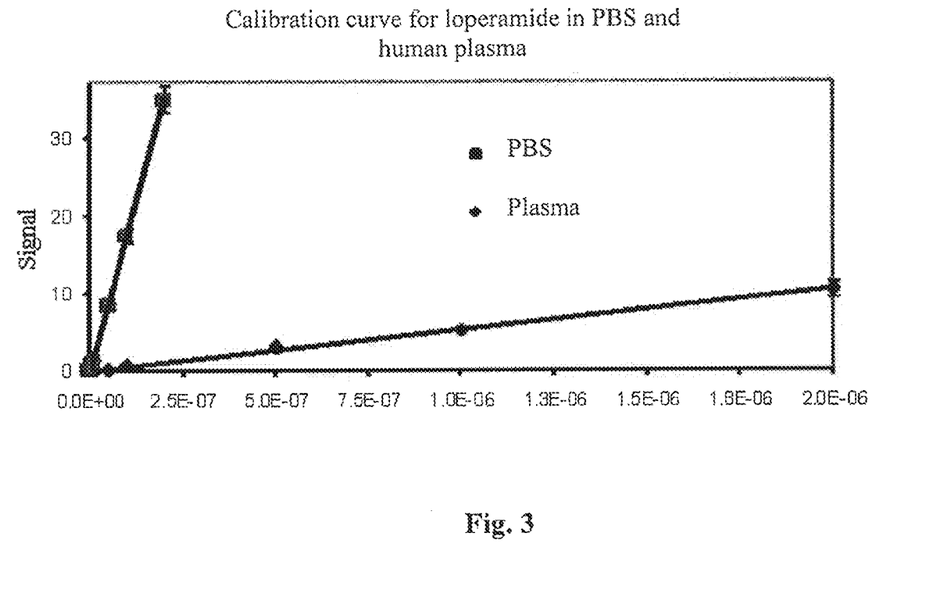
FIG. 3 shows calibration curves for extraction of loperamide, in two different matrixes, using a coating of an exemplary embodiment.

Various SPME coatings were investigated by studying the extraction and separation of drugs from human plasma. As shown in FIG. 3, a very good linear relationship was obtained for a seven point calibration (n=3). FIG. 3 also indicates that drug binding to plasma proteins changes the amount of drug available for extraction and results in different calibration slopes for plasma and PBS.

The linear range covered more than three orders of magnitude for most drugs, with the exception of warfarin, where the linear range spanned over two orders of magnitude. The fall details are shown in Table 2.

TABLE 2

Linear ranges for SPME-based analytical method.

| Linear Range (moles/L) | PAN/C-18 | | PAN/RP-amide | |
|---|---|---|---|---|
| | PBS | Plasma | PBS | Plasma |
| Diazepam | 1E−9−>2E−6 | 1E−8−>1E−5 | 3E−9−>1E−6 | 5E−8−>1E−5 |
| Verapamil | 1E−9−>1E−6 | 5E−9−>5E−6 | 2E−9−>4E−7 | 2E−8−>4E−6 |
| Warfarin | 2E−8−>5E−6 | 2E−7−>5E−5 | 2E−8−>4E−6 | 1E−6−>4E−5 |
| Nordiazepam | 1E−8−>5E−6 | 1E−7−>2E−5 | 7E−9−>2E−6 | 2E−7−>2E−5 |
| Loperamide | 1E−9−>2E−7 | 5E−9−>2E−6 | 2E−9−>2E−7 | 2E−8−>2E−6 |

The determination of plasma protein binding by SPME is based on determining the free concentration of drug in the presence of plasma proteins. Briefly, the percentage of drug binding to plasma proteins (PPB) is calculated from the total and free concentration of drug:

$$PPB\% = \frac{C_{total\ plasma} - C_{free\ plasma}}{C_{total\ plasma}} \cdot 100 = \left(1 - \frac{C_{free\ plasma}}{C_{total\ plasma}}\right) \cdot 100 \quad (1)$$

where $C_{total\ plasma}$ is the total concentration of drug in plasma and $C_{free\ plasma}$ is the free concentration of drug in plasma.

Considering that the total drug concentration is directly proportional to the slope of the drug calibration curve in PBS and the free concentration is directly proportional to the slope of plasma calibration, Equation 1 becomes:

$$PPB\% = 100 \cdot \left(1 - \frac{\text{slope calibration plasma}}{\text{slope calibration } PBS}\right) \quad (2)$$

Equation 2 was applied for the determination of drug plasma protein binding for the five test drugs, and the results are presented in Table 3. Only the most reproducible coatings were used, and the results correlate very well with previously published values.

TABLE 3

Experimental and literature drug plasma protein binding values.

| Plasma Protein Binding % | PAN/C-18 0.01", 60 μm | PAN/RP-amide 0.01", 60 μm | Literature Values (range) |
|---|---|---|---|
| Diazepam | 98 | 99 | 96-98 |
| Verapamil | 96 | 96 | 88-98 |
| Warfarin | 99 | 99 | 98-100 |
| Nordiazepam | 98 | 98 | 97-98 |
| Loperamide | 96 | 97 | 95-97 |

For the extraction efficiency test, the PAN coatings based on C-18, RP-amide and HS-F5 showed, on average, much higher extraction efficiency towards the investigated drugs: ~90 times more than PPY, ~50 times more than RAM or PDMS coatings, and ~20 times more than commercially available CW/TPR.

The above-described embodiments are intended to be examples only. Alterations, modifications and variations may be effected to the particular embodiments by those of skill in the art without departing from the scope of the disclosure, which is defined solely by the claims appended hereto.

The invention claimed is:

1. A method for measuring or identifying a small molecule component of interest in a biological system, the method comprising:
    positioning a fibre within the biological system, the fibre being at least partially coated with a polymeric extraction phase for adsorbing the small molecule component of interest from the biological system, the extraction phase being positioned within the biological system;
    adsorbing the small molecule component of interest onto the extraction phase;
    removing the fibre from the biological system;
    inserting the fibre into a nanospray needle;
    flowing solvent through the nanospray needle that has the fibre inserted therein;
    desorbing the small molecule component of interest from the extraction phase into the solvent flowing through the nanospray needle;
    nebulizing and electrospraying the desorbed small molecule component of interest in a solvent plume in the presence of an ionization source at atmospheric pressure to spray aerosolized ionized droplets out of the nanospray needle that has the fibre inserted therein and into an analytical instrument for measurement or identification; and measuring or identifying the small molecule component of interest present in the aerosolized ionized droplets in said analytical instrument.

2. The method according to claim 1, wherein the biological system is an animal or an animal tissue.

3. The method according to claim 2, wherein the animal is a mouse, rat, rabbit, dog, sheep, pig, monkey, or human.

4. The method according to claim 2, wherein the animal tissue is a live egg or an organ, or comprises a plurality of isolated cells.

5. The method according to claim 1, wherein the biological system is a sample collected from an animal or an animal tissue.

6. The method according to claim 5, wherein the animal is a mouse, rat, rabbit, dog, sheep, pig, monkey, or human.

7. The method according to claim 5, wherein the animal tissue is a live egg or an organ, or comprises a plurality of isolated cells.

8. The method according to claim 1, wherein the fibre is a flexible wire.

9. The method according to claim 1, wherein the extraction phase is loaded with a calibrant prior to sampling.

10. The method according to claim 1, wherein the coated end of the fibre is further coated with a polymeric biocompatible protection layer.

11. The method of claim 10, wherein the biocompatible protection layer comprises polypyrrole or derivatised cellulose.

12. The method of claim 1, wherein the polymeric extraction phase comprises substituted or unsubstituted poly (dimethylsiloxane), polyacrylate, poly (ethylene glycol), poly (divinylbenzene) or polypyrrole.

13. The method of claim 1, wherein the polymeric extraction phase additionally comprises a bioaffinity agent selected from the group consisting of a selective cavity, a molecular recognition moiety, a molecularly imprinted polymer and an immobilized antibody.

14. The method of claim 1, wherein the polymeric extraction phase comprises substituted or unsubstituted poly(divinylbenzene).

15. The method of claim 10, wherein the biocompatible protection layer comprises polypyrrole.

16. The method of claim 1, wherein the polymeric extraction phase additionally comprises a bioaffinity agent that is a selective cavity.

* * * * *